US012071109B2

(12) United States Patent
Goemer et al.

(10) Patent No.: US 12,071,109 B2
(45) Date of Patent: Aug. 27, 2024

(54) RETRACTABLE SANITIZING APPARATUSES FOR TRAVERSING AND SANITIZING SURFACES OF A VEHICLE

(71) Applicant: Toyota Motor North America, Inc., Plano, TX (US)

(72) Inventors: David M. Goemer, Frisco, TX (US); Evan Vijithakumara, Frisco, TX (US); Imad Zahid, Carrollton, TX (US); Lou Pope, Flower Mound, TX (US); Yuho Kozu, Dallas, TX (US); Lizbeth Jurado, El Paso, TX (US)

(73) Assignee: Toyota Motor North America, Inc., Plano, TX (US)

( * ) Notice: Subject to any disclaimer, the term of this patent is extended or adjusted under 35 U.S.C. 154(b) by 648 days.

(21) Appl. No.: 17/235,249

(22) Filed: Apr. 20, 2021

(65) Prior Publication Data

US 2022/0332291 A1    Oct. 20, 2022

(51) Int. Cl.
*B60S 1/64* (2006.01)
*A47L 7/00* (2006.01)
(Continued)

(52) U.S. Cl.
CPC ............... *B60S 1/64* (2013.01); *A47L 7/0061* (2013.01); *A47L 7/0076* (2013.01); *A47L 9/2821* (2013.01); *A61L 2/04* (2013.01); *A61L 2/10* (2013.01); *A61L 2/202* (2013.01); *A61L 2/22* (2013.01); *A61L 2/26* (2013.01);
(Continued)

(58) Field of Classification Search
CPC ........ B60S 1/64; A47L 7/0061; A47L 7/0076; A47L 9/2821; A61L 2/04; A61L 2/10; A61L 2/202; A61L 2/22; A61L 2/26; A61L 2202/11; A61L 2202/14; A61L 2202/15; A61L 2202/17; A61L 2202/25; A61L 2/24; B60N 2/90; B60N 2/58
See application file for complete search history.

(56) References Cited

U.S. PATENT DOCUMENTS

2014/0059796 A1\* 3/2014 Boodaghians ......... B64D 11/00
250/455.11
2015/0064065 A1\* 3/2015 Kreitenberg ............. B25J 5/007
422/24
(Continued)

FOREIGN PATENT DOCUMENTS

CN          2761451 Y      3/2006
CN        202896237 U      4/2013
(Continued)

*Primary Examiner* — Regina M Yoo
(74) *Attorney, Agent, or Firm* — Dinsmore & Shohl LLP

(57) ABSTRACT

A retractable sanitizing apparatus for a vehicle including a return station, a sanitizing mechanism positionable between a first sanitizing position, a second sanitizing position, and a stowed position, the sanitizing mechanism positioned at the return station when in the stowed position, and a linkage member connecting the sanitizing mechanism to the return station and positioning the sanitizing mechanism between the first sanitizing position and the second sanitizing position, wherein the sanitizing mechanism sanitizes a surface of the vehicle as the sanitizing mechanism moves from the first sanitizing position to the second sanitizing position and across the surface of the vehicle.

11 Claims, 4 Drawing Sheets

(51) Int. Cl.
*A47L 9/28* (2006.01)
*A61L 2/04* (2006.01)
*A61L 2/10* (2006.01)
*A61L 2/20* (2006.01)
*A61L 2/22* (2006.01)
*A61L 2/26* (2006.01)

(52) U.S. Cl.
CPC ........ *A61L 2202/11* (2013.01); *A61L 2202/14* (2013.01); *A61L 2202/15* (2013.01); *A61L 2202/17* (2013.01); *A61L 2202/25* (2013.01)

(56) References Cited

U.S. PATENT DOCUMENTS

| | | | |
|---|---|---|---|
| 2017/0297537 A1* | 10/2017 | Yako | B60N 2/90 |
| 2018/0064833 A1* | 3/2018 | Childress | A61L 2/10 |
| 2018/0214591 A1* | 8/2018 | Park | B64F 5/30 |
| 2018/0256764 A1* | 9/2018 | Kreitenberg | A61L 9/20 |
| 2019/0176768 A1 | 6/2019 | Diaz Garcia | |
| 2020/0198445 A1 | 6/2020 | Line et al. | |
| 2020/0269738 A1 | 8/2020 | Line et al. | |
| 2021/0308306 A1* | 10/2021 | Kreitenberg | A61L 2/26 |
| 2021/0346541 A1* | 11/2021 | Callahan | A61L 2/10 |
| 2021/0387729 A1* | 12/2021 | Subramanian | B64D 11/0606 |
| 2022/0023467 A1* | 1/2022 | Garner | A61L 2/10 |
| 2022/0047734 A1* | 2/2022 | Michalakos | A61L 2/10 |
| 2022/0111096 A1* | 4/2022 | Childress | A61L 2/26 |
| 2022/0152237 A1* | 5/2022 | Barrios Sierra | A61L 9/20 |
| 2022/0193283 A1* | 6/2022 | Meskimen | B60Q 3/233 |
| 2022/0193289 A1* | 6/2022 | Omohundro | B05B 5/085 |
| 2022/0219584 A1* | 7/2022 | Ketels | A61L 9/18 |
| 2023/0218793 A1* | 7/2023 | Spillner | A61L 2/18 15/302 |
| 2023/0310684 A1* | 10/2023 | Rister | B64U 10/13 422/24 |

FOREIGN PATENT DOCUMENTS

| | | |
|---|---|---|
| CN | 207072331 U | 3/2016 |
| CN | 109263439 A | 1/2019 |
| CN | 109484364 A | 3/2019 |
| CN | 208591353 U | 3/2019 |
| CN | 109908388 A | 6/2019 |
| CN | 110065475 A | 7/2019 |
| CN | 209063855 U | 7/2019 |
| DE | 202009013605 U1 | 3/2010 |
| DE | 102016215247 A1 | 2/2018 |
| EP | 3402686 A1 | 11/2018 |
| IN | 201741022536 A | 1/2019 |
| JP | 2006341759 A | 12/2006 |
| WO | 2019139743 A1 | 7/2019 |

* cited by examiner

RETRACTABLE SANITIZING APPARATUSES FOR TRAVERSING AND SANITIZING SURFACES OF A VEHICLE

TECHNICAL FIELD

The present specification generally relates to systems and methods for sanitizing an interior surface of a vehicle and, more specifically, systems and methods for sanitizing an interior surface of a vehicle by traversing a sanitizing mechanism across the interior surface of the vehicle.

BACKGROUND

Vehicle surfaces can become contaminated after prolonged use and contact by occupants or other objects that may carry some amount of contaminants. This is particularly common in vehicles in which different occupants are regularly entering and exiting the vehicle such as, for example, in ridesharing vehicles. These surfaces, such as vehicle seats and other surfaces regularly contacted by these occupants, may be sanitized, for example, by manually applying, e.g., spraying, a sanitizing agent on the surface and disinfecting the surface. However, this requires a great deal of time and energy and interrupts the normal use of the vehicle in transporting an occupant that is unable to occupy the space being sanitized.

Accordingly, a need exists for improved systems and methods of sanitizing a surface of a vehicle by utilizing an automatically retractable sanitizing apparatus that traverses a surface of the vehicle without operator intervention.

SUMMARY

In one embodiment, a retractable sanitizing apparatus for a vehicle includes a return station, a sanitizing mechanism positionable between a first sanitizing position, a second sanitizing position, and a stowed position, the sanitizing mechanism positioned at the return station when in the stowed position, and a linkage member connecting the sanitizing mechanism to the return station and positioning the sanitizing mechanism between the first sanitizing position and the second sanitizing position, wherein the sanitizing mechanism sanitizes a surface of the vehicle as the sanitizing mechanism moves from the first sanitizing position to the second sanitizing position and across the surface of the vehicle.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
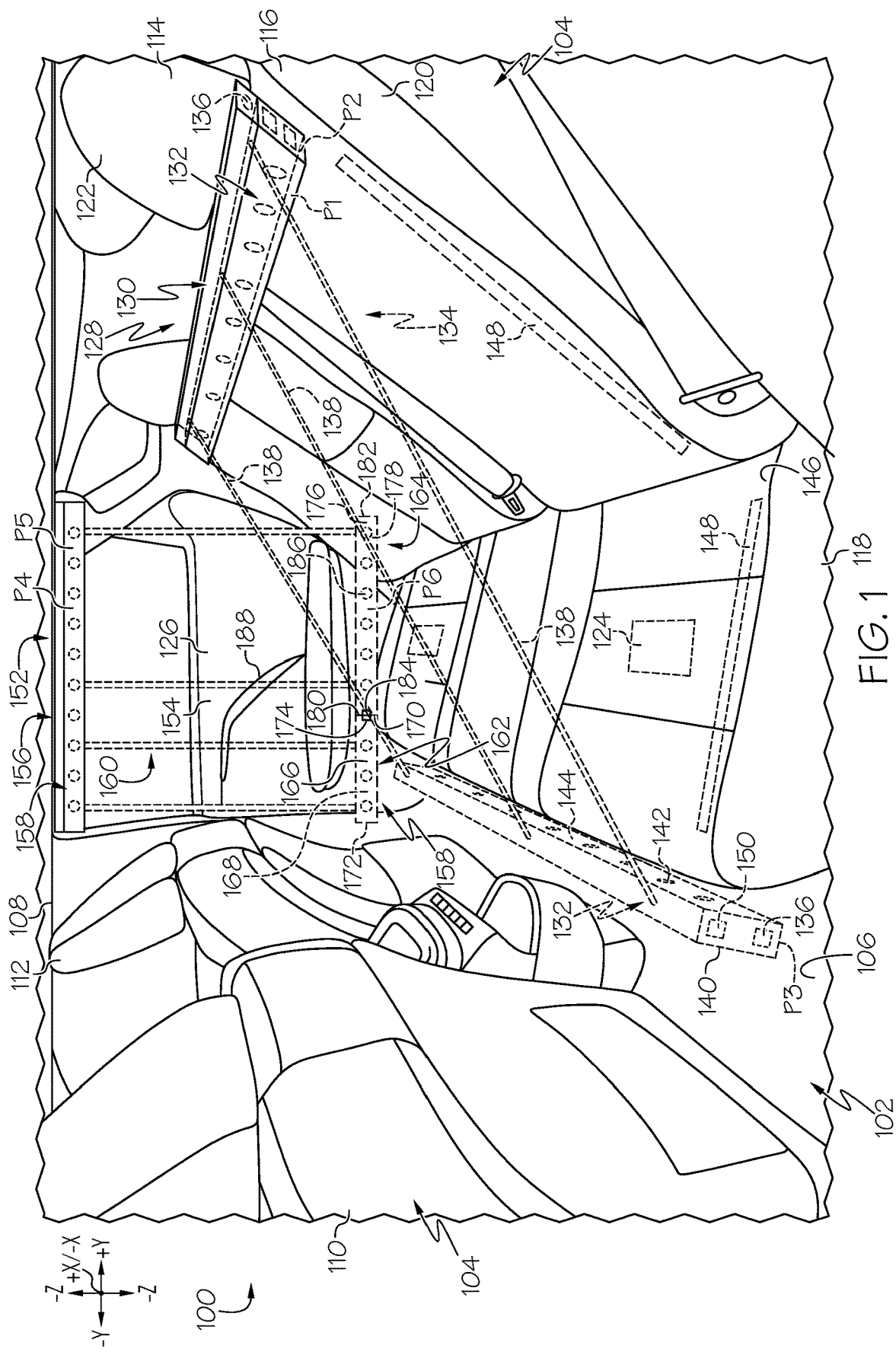
FIG. 1 schematically depicts a perspective view of a passenger compartment of a vehicle including a plurality of retractable sanitizing apparatuses in a first position, according to one or more embodiments shown and described herein.

Embodiments described herein are directed to a retractable sanitizing apparatus for a vehicle that includes a sanitizing mechanism that translates over a surface of the vehicle. The retractable sanitizing apparatus includes a return station, a sanitizing mechanism positionable between a first sanitizing position, a second sanitizing position, and a stowed position, and a linkage member connecting the sanitizing mechanism to the return station and positioning the sanitizing mechanism between the first sanitizing position and the second sanitizing position. Various embodiments of the retractable sanitizing apparatus and the operation of the retractable sanitizing apparatus are described in more detail herein. Whenever possible, the same reference numerals will be used throughout the drawings to refer to the same or like parts.

As used herein, the term "vehicle longitudinal direction" refers to the forward-rearward direction of the vehicle (i.e., in the +/−Y direction of the coordinate axes depicted in FIG. 1). The term "vehicle lateral direction" refers to the cross-vehicle direction (i.e., in the +/−X direction of the coordinate axes depicted in FIG. 1), and is transverse to the vehicle longitudinal direction. The term "vehicle vertical direction" refers to the upward-downward direction of the vehicle (i.e., in the +/−Z direction of the coordinate axes depicted in FIG. 1). As used herein, "upper" and "above" are defined as the positive Z direction of the coordinate axes shown in the drawings. "Lower" and "below" are defined as the negative Z direction of the coordinate axes shown in the drawings.

Referring to FIG. 1, a vehicle 100 is generally illustrated. The vehicle 100 includes a passenger compartment 102 which passengers or other occupants occupy. As shown, a plurality of vehicle seats 104 are provided within the passenger compartment 102 of the vehicle 100 and mounted above a floor surface 106 of the vehicle 100. The floor surface and a ceiling 108 of the vehicle 100 at least partially define the passenger compartment 102 of the vehicle 100. The plurality of vehicle seats 104 may include a driver seat 110, a passenger seat 112, and a plurality of rear passenger seats 114 forming a rear bench seat 116. In embodiments, the rear bench seat 116 includes a seat cushion 118 mounted above the floor surface 106 of the vehicle 100, a seat back 120 pivotally attached to the seat cushion 118, and a headrest 122 mounted to an end of the seat back 120 opposite the seat cushion 118. In embodiments, the rear bench seat 116 may include one or more pressure sensors 124 located in the seat cushion 118 and/or the seat back 120 for detecting the presence of an occupant on the rear bench seat 116 based on the pressure sensor 124 detecting a pressure exceeding a predetermined threshold. As shown, the vehicle 100 also includes a rear door 126 located adjacent the rear bench seat 116 for providing access to the passenger compartment 102 of the vehicle 100.

As described in more detail herein, embodiments of retractable sanitizing apparatuses are provided for sanitizing a surface of the vehicle 100 between occupant uses such as, for example, a surface of one of the plurality of vehicle seats 104 and/or the rear door 126. In embodiments, the rear bench seat 116 may include a retractable sanitizing apparatus 128 or a plurality of retractable sanitizing apparatuses 128 for sanitizing one or more surfaces of the rear bench seat 116. However, it should be appreciated that the present disclosure is not limited to being utilized on the rear bench seat 116 and is equally applicable to other surfaces of the vehicle 100 that are regularly contacted by an occupant such as, for example, the rear door 126, a bucket seat, etc. In addition, it should be appreciated that although the vehicle 100 depicted herein is illustrated as an automobile, the vehicle 100 may be any other passenger or non-passenger vehicle such as, for example, a terrestrial, aquatic, and/or airborne vehicle.

Referring still to FIG. 1, in embodiments, the retractable sanitizing apparatus 128 is illustrated positioned on the rear bench seat 116. More particularly, the retractable sanitizing apparatus 128 includes a return station 130, a sanitizing mechanism 132, and a linkage member 134 connecting the sanitizing mechanism 132 to the return station 130. The linkage member 134 is operable to position the sanitizing mechanism 132 between a stowed position P1, a first sanitizing position P2, and a second sanitizing position P3. In embodiments, the stowed position P1 and the first sanitizing position P2 may be the same. As shown in FIG. 1, the sanitizing mechanism 132 is shown in the stowed position P1 and the first sanitizing position P2 by the sanitizing mechanism 132 illustrated in solid lines, and in the second sanitizing position P3 illustrated in dashed lines.

In embodiments, the return station 130 is mounted at or near an end of the seat back 120 of the rear bench seat 116 proximate the headrest 122. The return station 130 may function as a housing for various components of the retractable sanitizing apparatus 128 such as, for example, a motor 136 of the linkage member 134, a power supply, a control system 300, as discussed herein, and the like. As shown, the return station 130 may extend in the vehicle lateral direction and substantially along an entire width of the rear bench seat 116. In embodiments, the return station 130 may be mounted to the ceiling 108 of the vehicle 100.

The linkage member 134 may include one or more flexible, elongated members 138 extending between the return station 130 and the sanitizing mechanism 132. For ease of illustration, the elongated members 138 are shown in dashed lines in FIG. 1. In embodiments, the elongated members 138 may be a cord, strap, chain, sheet, or the like that can be retracted within the return station 130, such as by winding around a spool. As shown, three elongated members 138 extend between the return station 130 and the sanitizing mechanism 132 to control the movement of and stabilize the sanitizing mechanism 132. For example, the three elongated members 138 of the linkage member 134 may be configured to maintain the sanitizing mechanism 132 in a substantially vehicle lateral direction and parallel to a longitudinal axis of the return station 130 while moving relative to the return station 130. However, any number of elongated members 138 may be provided. In embodiments, the linkage member 134 may be positioned, i.e., housed, within the return station 130 when the sanitizing mechanism 132 is in the stowed position. Here, the motor 136, discussed herein as being provided within the return station 130, may be operated to control an amount of extension and retraction of the elongated members 138 from the return station 130, thereby controlling movement of the sanitizing mechanism 132 between the stowed position P1, the first position P2, and the second position P3 by adjusting the amount of extension of the linkage member 134 from the return station 130. Alternatively, the motor 136 and the elongated members 138 may be positionable within the sanitizing mechanism 132 itself such that operation of the motor 136 causes extension and/or retraction of the elongated members 138 from the sanitizing mechanism 132 and permits the sanitizing mechanism 132 to move between the stowed position P1, the first sanitizing position P2, and the second sanitizing position P3.

In embodiments, the linkage member 134 may determine a total length of travel of the sanitizing mechanism 132 based on operating parameters of the linkage member 134 such as, for example, speed of the motor 136, operating time of the motor 136, and the like. This information may be utilized to identify a position of the sanitizing mechanism 132 at any given time and determine how the sanitizing mechanism 132 should be operated between the first sanitizing position P2 and the second sanitizing position P3, as discussed in more detail herein.

In embodiments, the sanitizing mechanism 132 may be permitted to be manually drawn from the return station 130 when in the stowed position P1 toward the second sanitizing position P3 by an occupant pulling the sanitizing mechanism 132. In this case, the motor 136 operates to return the sanitizing mechanism 132 to the first sanitizing position P2 and, subsequently, the stowed position P1 from the second sanitizing position P3 by retracting the elongated members 138 either within the return station 130 or the sanitizing mechanism 132.

Figure 2:
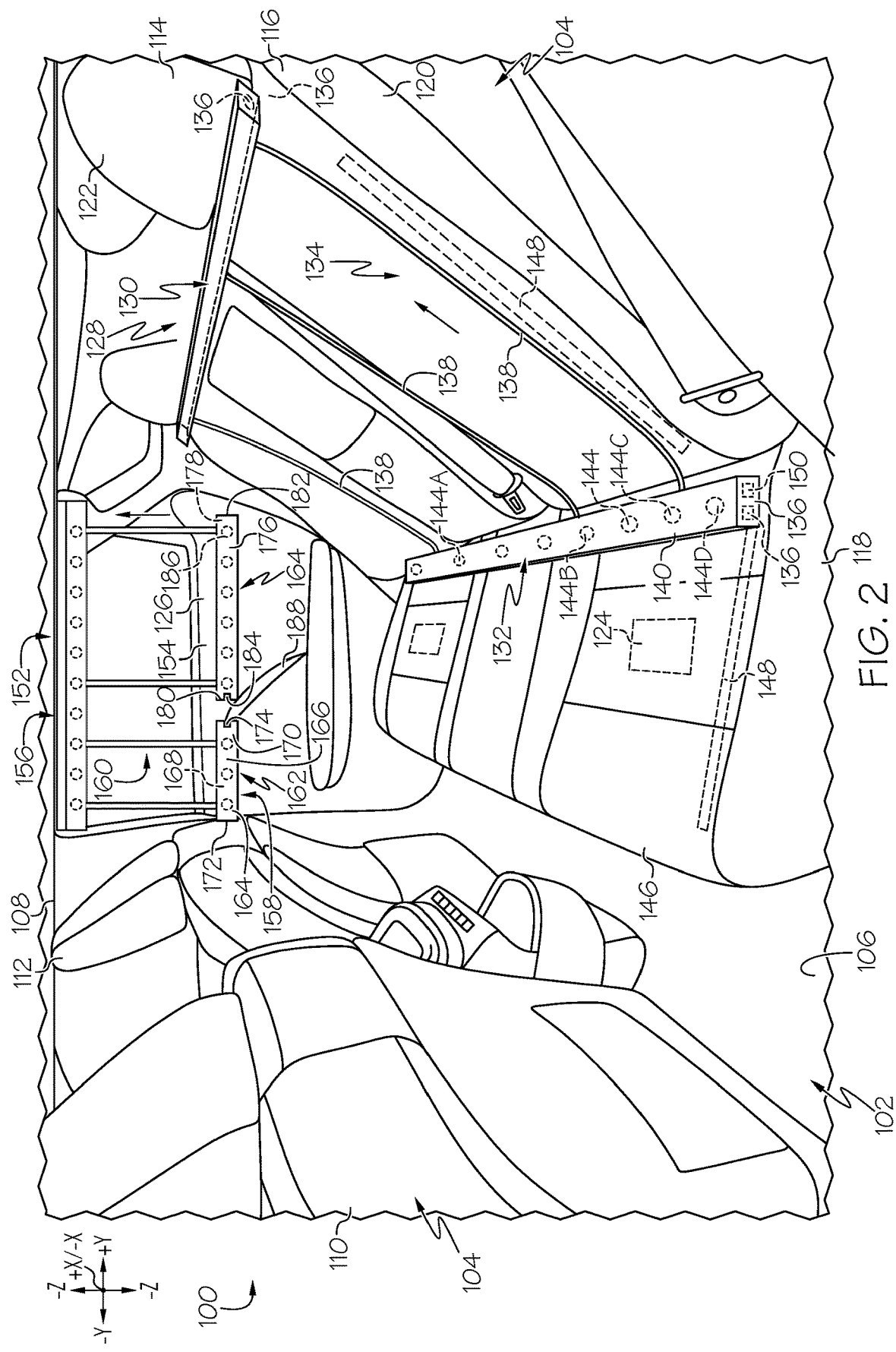
FIG. 2 schematically depicts a perspective view of the passenger compartment of the vehicle including the plurality of retractable sanitizing apparatuses in another position, according to one or more embodiments shown and described herein.

In embodiments, the sanitizing mechanism 132 includes a first side 140 and an opposite second side 142. The second side 142 of the sanitizing mechanism 132 is oriented to face the surface of the vehicle 100 to be sanitized, for example, the rear bench seat 116. The sanitizing mechanism 132 may include one or more sanitizing devices 144 provided on the second side 142 of the sanitizing mechanism 132 for directing a sanitizing agent toward a surface of the rear bench seat defined by the seat cushion 118 and the seat back 120. As shown, the sanitizing mechanism 132 includes a plurality of sanitizing devices 144 provided on the second side 142 thereof. In embodiments, as shown in FIG. 2, one or more of the sanitizing devices 144 may include a drying device 144A, such as an ultraviolet or high temperature heat lamp, one or more of the sanitizing devices 144 may include a sanitizing spray nozzle 144B for emitting a solution, one or more of the sanitizing devices 144 may include an ozone emitter 144C, and one or more of the sanitizing devices 144 may include a vacuum 144D. Accordingly, the sanitizing mechanism 132 may include any combination of sanitizing devices 144 for sanitizing the surface 146 of the rear bench seat 116 in various manners. As shown, the plurality of sanitizing devices 144 extend along a substantially entire length of the sanitizing mechanism 132 to cover a substantial length of the rear bench seat 116 when positioned adjacent the second side 142 of the sanitizing mechanism 132. Alternatively, a single sanitizing device 144, such as a single drying device 144A, spray nozzle 144B, ozone emitter 144C, or vacuum 144D may be formed to extend along a substantial portion of the length of the second side 142 of the sanitizing mechanism 132.

In embodiments, the rear bench seat 116 may include a magnetic track 148 extending along the surface 146 of the rear bench seat 116, for example, within the seat cushion 118 and/or the seat back 120, which cooperates with one or more magnets 150 provided at or near the second side 142 of the sanitizing mechanism 132. Thus, the second side 142 of the sanitizing mechanism 132 is attracted to the magnetic track 148 in the rear bench seat 116 as the sanitizing mechanism 132 traverses the rear bench seat 116 when moving between the second sanitizing position P3 and the first sanitizing position P2.

As shown in FIG. 2, the sanitizing mechanism 132 is illustrating moving from the second sanitizing position P3 toward the first sanitizing position P2. Thus, the sanitizing mechanism 132 is located at an intermediate position between the first sanitizing position P2 and the second sanitizing position P3 after sanitizing the seat cushion 118 of the rear bench seat 116.

Referring again to FIG. 1, an embodiment of a retractable sanitizing apparatus 152 is illustrated for sanitizing a surface 154 of the door 126 of the vehicle 100. The retractable sanitizing apparatus 152 at the door 126 is substantially similar to the retractable sanitizing apparatus 128 on the rear bench seat 116. Accordingly, the retractable sanitizing apparatus 152 includes a return station 156, a sanitizing mechanism 158, and a linkage member 160 connecting the sanitizing mechanism 158 to the return station 156. The return station 156 may be mounted to the ceiling 108 of the vehicle 100 such that the sanitizing mechanism 158 is capable of extending along a front surface of the door 126, as discussed herein. Alternatively, the return station 156 may be mounted to the door 126 of the vehicle 100 itself or a frame of the vehicle 100 between the ceiling 108 and the door 126. The linkage member 160 is operable to position the sanitizing mechanism 158 between a stowed position P4, a first sanitizing position P5, and a second sanitizing position P6. In embodiments, the stowed position P4 and the first sanitizing position P5 may be the same. As shown in FIG. 1, the sanitizing mechanism 158 is shown in the stowed position P4 and the first sanitizing position P5 by the sanitizing mechanism 158 illustrated in solid lines, and in the second sanitizing position P6 illustrated in dashed lines. Thus, when the sanitizing mechanism 158 is in the stowed position P4, the sanitizing mechanism is located at the return station 156, such as at the ceiling 108, the door 126, or a frame member of the vehicle 100 between the ceiling 106 and the door 126.

The return station 156, the sanitizing mechanism 158, and the linkage member 160 may include each of the features of the return station 130, the sanitizing mechanism 132, and the linkage member 134, respectively, of the retractable sanitizing apparatus 128 of the rear bench seat 116 discussed herein. However, in embodiments, the sanitizing mechanism 158 includes a first sanitizing mechanism portion 162 and a second sanitizing mechanism portion 164 that are temporarily separable from one another, which allows the sanitizing mechanism 158 to sanitize surfaces of the door 126 extending along different planes in the vehicle lateral direction.

With more particularity, the first sanitizing mechanism portion 162 includes a first side 166 facing the passenger compartment 102, an opposite second side 168 facing the surface 154 of the door 126 to be sanitized, a first end 170, and an opposite second end 172. In embodiments, the first sanitizing mechanism portion 162 includes a first magnet 174 provided at the first end 170 thereof. Similarly, the second sanitizing mechanism portion 164 includes a first side 176 facing the passenger compartment 102, an opposite second side 178 facing the surface 154 of the door 126 to be sanitized, a first end 180, and an opposite second end 182. In embodiments, the second sanitizing mechanism portion 164 includes a second magnet 184 provided at the first end 180 thereof. The first magnet 174 and the second magnet 184 cause the first end 170 of the first sanitizing mechanism portion 162 to be attracted to the first end 180 of the second sanitizing mechanism portion 164. As with the sanitizing mechanism 132 discussed herein, the first sanitizing mechanism portion 162 and the second sanitizing mechanism portion 164 each include one or more sanitizing devices 186 for emitting a sanitizing agent at the surface 154 of the vehicle 100 to be sanitized.

Although referred to herein as the first magnet 174 and the second magnet 184, it should be appreciated that other manners for coupling the first sanitizing mechanism portion 162 and the second sanitizing mechanism portion 164 are contemplated as being within the scope of the present disclosure. For example, buckles, latches, clasps, and the like may be provided at the first ends 170, 180 of the first sanitizing mechanism portion 162 and the second sanitizing mechanism portion 164, respectively, to fix the two to one another.

Accordingly, when the first sanitizing mechanism portion 162 and the second sanitizing mechanism portion 164 are positioned against surfaces extending in the same, or substantially similar, plane in the vehicle lateral direction, the first end 170 of the first sanitizing mechanism portion 162 and the first end 180 of the second sanitizing mechanism portion 164 remain in contact with one another. However, when the first sanitizing mechanism portion 162 and the second sanitizing mechanism portion 164 are positioned against surfaces that do not extend in the same, or substantially similar, plane in the vehicle lateral direction, one of the first sanitizing mechanism portion 162 and the second sanitizing mechanism portion 164 may be pushed in the vehicle lateral direction and away from the other of the first sanitizing mechanism portion 162 and the second sanitizing mechanism portion 164.

For example, as shown in FIG. 2, the sanitizing mechanism 158 is shown moving from the second sanitizing position P6 toward the first sanitizing position P5 and the stowed position P4 and contacting an obstacle, such as a door handle 188, on the door 126 of the vehicle 100. Specifically, the first sanitizing mechanism portion 162 contacts the door handle 188, which pushes the first sanitizing mechanism portion 162 further into the passenger compartment 102 of the vehicle 100 in the vehicle lateral direction and, thus, causes the first sanitizing mechanism portion 162 to move out of contact with the second sanitizing mechanism portion 164. This allows the first sanitizing mechanism portion 162 and the second sanitizing mechanism portion 164 to continue cleaning one or more surfaces of the door 126 that are not coplanar with one another without unnecessarily moving a portion of the sanitizing mechanism 158 out of contact with the surface 154 of the door 126.

Referring again to FIG. 1, in the present example, once the first sanitizing mechanism portion 162 is moved above the handle 188 and the surface 154 to be sanitized by each are substantially coplanar, the first sanitizing mechanism portion 162 and the second sanitizing mechanism portion 164, specifically the first ends 170, 180 thereof, are attracted to one another again to join the first sanitizing mechanism portion 162 and the second sanitizing mechanism portion 164.

Figure 3:
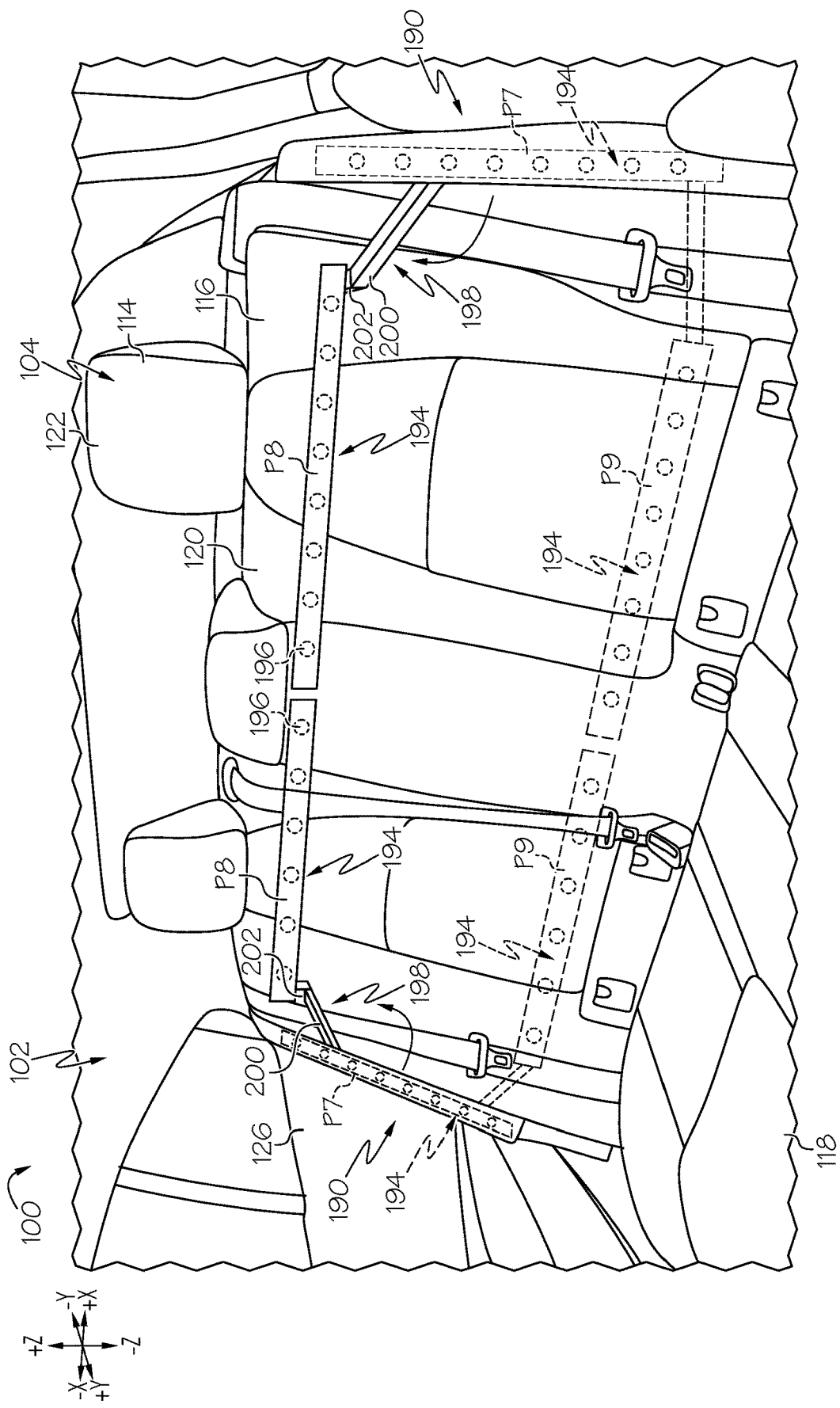
FIG. 3 schematically depicts a perspective view of an embodiment of a retractable sanitizing apparatus on a rear bench seat, according to one or more embodiments shown and described herein.

Referring now to FIG. 3, another embodiment of a retractable sanitizing apparatus 190 is shown on the rear bench seat 116. More particularly, a pair of retractable sanitizing apparatuses 190 are shown on the rear bench seat 116 such that one retractable sanitizing apparatus 190 sanitizes a first half of the rear bench seat 116 and the other retractable sanitizing apparatus 190 sanitizes the other half of the rear bench seat 116. This reduces the size of the retractable sanitizing apparatus 190 and, thus, reduces the strain when moving the retractable sanitizing apparatus 190 between sanitizing positions, as discussed herein.

The retractable sanitizing apparatus 190 is substantially similar to the retractable sanitizing apparatus 128. Accordingly, the retractable sanitizing apparatus 190 includes a return station 192, a sanitizing mechanism 194 including one or more sanitizing devices 196, and a linkage member 198 connecting the sanitizing mechanism 194 to the return station 192. The linkage member 198 is operable to position the sanitizing mechanism 194 between a stowed position P7, a first sanitizing position P8, and a second sanitizing position P9. As shown in FIG. 3, the sanitizing mechanism 194 is shown in the stowed position P7 illustrated in dashed lines within the return station 192, in the first sanitizing position P8 illustrated in solid lines, and in the second sanitizing position P9 illustrated in dashed lines outside of the return station 192.

As shown in FIG. 3, the return station 192 is provided at an end of the rear bench seat 116 and extends in a substantially vehicle vertical direction along the seat back 120 of the rear bench seat 116. Further, it should be appreciated that the return station 192 may be configured to house the linkage member 198 and the sanitizing mechanism 194 when the sanitizing mechanism 194 is the stowed position P7. Thus, the retractable sanitizing apparatus 190 may occupy less space at the end of the rear bench seat 116 as would be the case when the sanitizing mechanism 194 is positioned at the return station 192, rather than within the return station 192, when in the stowed position P7.

In the present embodiment, the linkage member 198 may be an arm 200 including one or more joints 202 for pivoting the sanitizing mechanism 194 between the stowed position P7, the first sanitizing position P8, and the second sanitizing position P9. Once the sanitizing mechanism 194 is pivoted into, for example, the first sanitizing position P8, the linkage member 198 is then capable of moving the sanitizing mechanism 194 toward the second sanitizing position P9, or vice versa, at which time the sanitizing mechanism 194 is operated to deliver the sanitizing agent onto the rear bench seat 116. Although the sanitizing mechanism 194 is only shown as being positionable along the seat back 120 of the rear bench seat 116, it should be appreciated that the linkage member 198 may be configured, such as by increasing the length thereof or the number of joints 202, to permit the sanitizing mechanism 194 to extend across the seat cushion 118 of the rear bench seat 116.

It should be appreciated that the various embodiments discussed herein are provided for illustrative purposes only and not intended to be limiting to the present disclosure. Specifically, it is within the scope of the present disclosure that the various embodiments discussed herein may be provided at any suitable location of the vehicle 100 as opposed to the rear bench seat 116 and the door 126 detailed herein. As further non-limiting examples, the present disclosure is equally applicable to any suitable location of the vehicle 100. Furthermore, the features of the embodiments of the retractable sanitizing apparatuses 128, 152, 190 discussed herein are not exclusive of one another and may be combined in any suitable arrangement.

Figure 4:
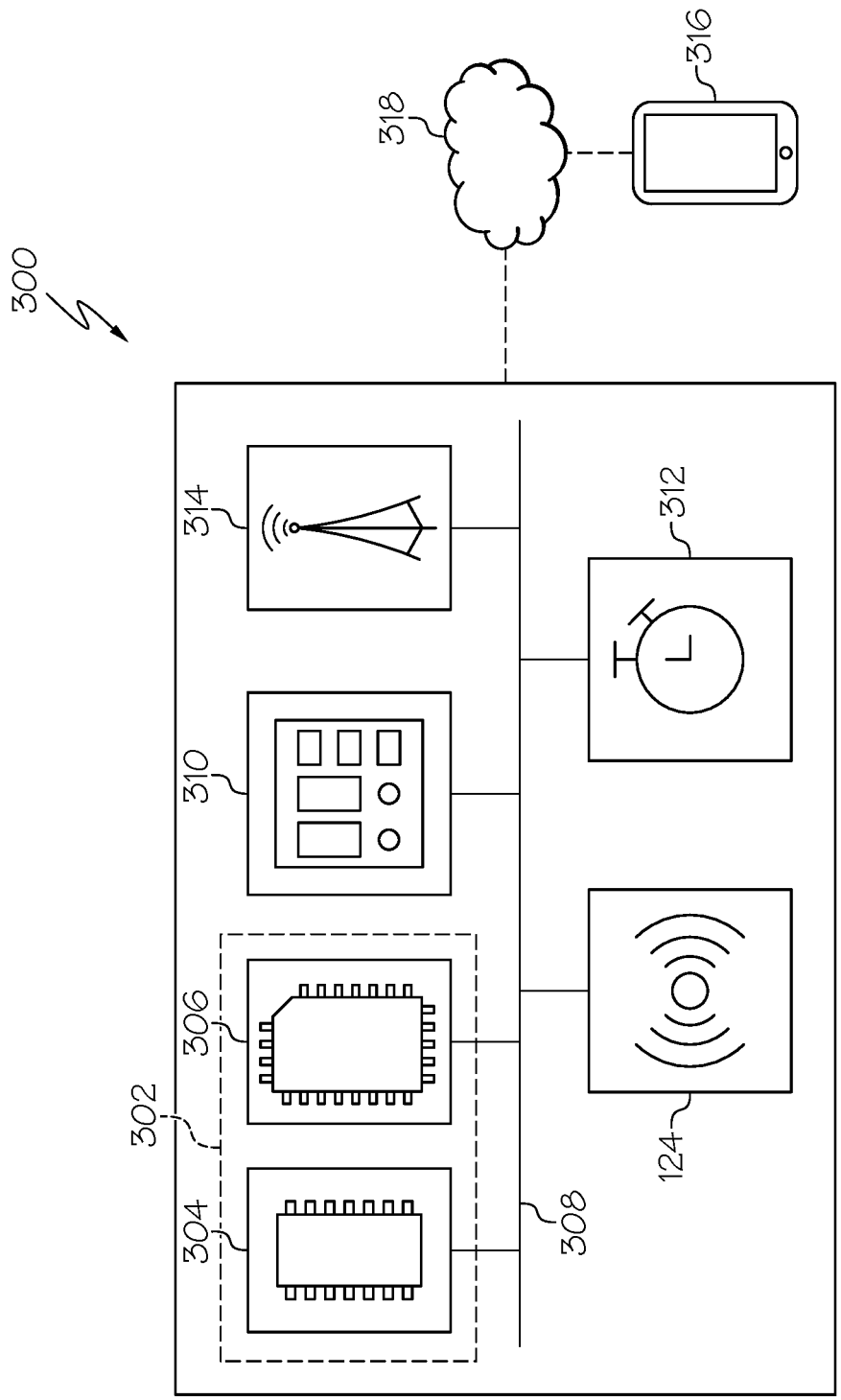
FIG. 4 schematically depicts a control system for operating a retractable sanitizing apparatus, according to one or more embodiments shown and described herein.

Referring now to FIG. 4, and with reference to the vehicle 100 illustrated in FIGS. 1-3, a schematic diagram of a control system 300 for operating one or more of the retractable sanitizing apparatuses 128, 152, 190 discussed herein is depicted. While the control system 300 is depicted in isolation, the control system 300 may be included within the vehicle 100 of FIG. 1. Without limiting the present disclosure, reference to the operation of the control system 300 may be made to the control system 300 operating the retractable sanitizing apparatus 128. However, operation of the control system 300 is equally applicable to the other embodiments discussed herein.

The control system 300 includes a controller 302 including one or more processors 304 and one or more memory modules 306. Each of the one or more processors 304 may be any device capable of executing machine readable and executable instructions. Accordingly, each of the one or more processors 304 may be an integrated circuit, a microchip, a computer, or any other computing device. The one or more processors 304 are coupled to a communication path 308 that provides signal interconnectivity between various modules of the control system 300. Accordingly, the communication path 308 may communicatively couple any number of processors 304 with one another, and allow the modules coupled to the communication path 308 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 308 may be formed from any medium that is capable of transmitting a signal such as, for example, conductive wires, conductive traces, optical waveguides, or the like. In some embodiments, the communication path 408 may facilitate the transmission of wireless signals, such as WiFi, Bluetooth®, Near Field Communication (NFC) and the like. Moreover, the communication path 308 may be formed from a combination of mediums capable of transmitting signals. In one embodiment, the communication path 308 comprises a combination of conductive traces, conductive wires, connectors, and buses that cooperate to permit the transmission of electrical data signals to components such as processors, memories, sensors, input devices, output devices, and communication devices. Accordingly, the communication path 308 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

As noted above, the control system 300 includes one or more memory modules 306 coupled to the communication path 308. The one or more memory modules 306 may comprise RAM, ROM, flash memories, hard drives, or any device capable of storing machine readable and executable instructions such that the machine readable and executable instructions can be accessed by the one or more processors 304. The machine readable and executable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable and executable instructions and stored on the one or more memory modules 306. Alternatively, the machine readable and executable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

As noted above, the linkage member 134 of the retractable sanitizing apparatus 128, for example, may be configured to identify a position of the sanitizing mechanism 132 based on operating parameters, such as operating speed, length of time, etc. This information may be utilized to determine when to activate and deactivate the sanitizing mechanism 132 and, more particularly, alternatingly operate individual sanitizing devices 144 of the sanitizing mechanism 132 based on machine readable instructions stored in the one or more memory modules 306. For example, a first subset of the sanitizing devices 144 including, for example, the vacuum 144D, may be operated when it is determined that the sanitizing mechanism 132 is at a first location between the first sanitizing position P2 and the second sanitizing position P3, a second subset of the sanitizing devices 144 including, for example, the spray nozzles 144B, may be operated when it is determined that the sanitizing mechanism 132 is at a second location between the first sanitizing position P2 and the second sanitizing position P3, and a third subset of the sanitizing devices 144 including, for example, the high temperature heat lamp 144A, may be operated when it is determined that the sanitizing mechanism 132 is at a third location between the first sanitizing position P2 and the second sanitizing position P3.

The control system 300 also includes the user control device 310 coupled to the communication path 308. The user control device 310 includes one or more controls for manually operating the retractable sanitizing apparatuses 128, 152, 190. More particularly, with respect to the retractable sanitizing apparatus 128, the controls of the user control device 310 may be utilized to initiate actuation of the linkage member 134 to position the sanitizing mechanism 132 and, thereafter, actuate the sanitizing mechanism 132. The one or more controls of the user control device 310 may include, for example, buttons or the like. In some embodiments, the user control device 310 includes a user interface, such as a touch screen user interface. As such, the user control device 310 may be included or incorporated into a display device.

In embodiments, the control system 300 includes the pressure sensor 124 within the seat cushion 118 of the rear bench seat 116, discussed herein, which is coupled to the communication path 308 for monitoring the presence of an occupant in the rear bench seat 116. The pressure sensor 124 may determine that an occupant is not present in the rear bench seat 116 when the pressure sensor 124 detects a pressure below a predetermined threshold. For example, in response to the pressure sensor 124 determining that an occupant is no longer seated in the rear bench seat 116, the retractable sanitizing apparatus 128, for example, may be operated to automatically operate the linkage member 134 and actuate the sanitizing mechanism 132 in the manner discussed herein.

In embodiments, the control system 300 includes a timer 312 coupled to the communication path 308. The timer 312 may be utilized for automatically operating the retractable sanitizing apparatuses 128, 152, 190 after a predetermined period of time. For example, in response to determining that no occupant is present within the rear bench seat 116 and a predetermined period of time has elapsed, the retractable sanitizing apparatus 128, for example, may be operated to automatically operate the linkage member 134 such that the sanitizing mechanism 132 is moved to the second sanitizing position P3, the sanitizing mechanism 132 is actuated to emit the sanitizing agent, and the sanitizing mechanism 132 is subsequently moved toward the first sanitizing position P2 to sanitize the surface 146 of the rear bench seat 116.

In embodiments, the control system 300 includes network interface hardware 314 for communicatively coupling the control system 300 to a remote device 316 such as, for example, a mobile device, via a network 318. The network interface hardware 314 can be communicatively coupled to the communication path 308 and can be any device capable of receiving and transmitting data via the network 318. Accordingly, the network interface hardware 314 can include a communication transceiver for sending and/or receiving any wired or wireless communication. For example, the network interface hardware 314 may include an antenna, a modem, LAN port, Wi-Fi card, WiMax card, mobile communications hardware, near-field communication hardware, satellite communication hardware and/or any wired or wireless hardware for communicating with other networks and/or devices. In one embodiment, the network interface hardware 314 includes hardware configured to operate in accordance with the Bluetooth® wireless communication protocol. For example, the network interface hardware 314 of the control system 300 may receive an instruction from the remote device 316 and, subsequently, transmit the instruction to the retractable sanitizing apparatuses 128, 152, 190 to operate in response to receiving the instruction.

From the above, it is to be appreciated that defined herein is a retractable sanitizing apparatus for a vehicle that translates across a surface of a vehicle. Accordingly, the surface of the vehicle may be automatically sanitized without user intervention and wherein the retractable sanitizing apparatus may be positioned into a stowed position when not in use.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A retractable sanitizing apparatus for a vehicle comprising:
   a return station mounted at one of an upper end of a seat back of the vehicle and an upper end of a door of the vehicle;
   a sanitizing mechanism positionable between a first sanitizing position, a second sanitizing position, and a stowed position, the sanitizing mechanism positioned at the return station when in the stowed position; and
   a linkage member connecting the sanitizing mechanism to the return station and positioning the sanitizing mechanism between the first sanitizing position and the second sanitizing position,
   wherein the sanitizing mechanism sanitizes a surface of the vehicle as the sanitizing mechanism moves from the first sanitizing position to the second sanitizing position and across the surface of the vehicle.

2. The retractable sanitizing apparatus of claim 1, wherein a motor is provided within one of the return station and the sanitizing mechanism for operating the linkage member and controlling movement of the sanitizing mechanism between the first sanitizing position and the second sanitizing position.

3. The retractable sanitizing apparatus of claim 2, wherein:
the linkage member comprises a flexible, elongated member that retracts within one of the return station and the sanitizing mechanism when the sanitizing mechanism is in the stowed position; and
the sanitizing mechanism extends parallel to the return station when in the first sanitizing position and the second sanitizing position.

4. The retractable sanitizing apparatus of claim 2, further comprising:
a pressure sensor; and
a controller configured to:
operate the motor to control the linkage member and movement of the sanitizing mechanism between the stowed position, the first sanitizing position, and the second sanitizing position in response to the pressure sensor not detecting a pressure exceeding a predetermined threshold.

5. The retractable sanitizing apparatus of claim 4, wherein the sanitizing mechanism comprises one or more of an ultraviolet or heat lamp, a spray nozzle, an ozone emitter, and a vacuum.

6. The retractable sanitizing apparatus of claim 4, wherein:
the sanitizing mechanism comprises:
a vacuum;
one or more spray nozzles for spraying a sanitizing agent; and
a drying device,
the controller is configured to alternatingly operate the vacuum device, the one or more nozzles, and the drying device based on a position of the sanitizing mechanism between the first sanitizing position and the second sanitizing position.

7. The retractable sanitizing apparatus of claim 1, wherein the surface of the vehicle is a seat of the vehicle, the seat including the seat back and a seat cushion, and wherein the sanitizing mechanism traverses the seat of the vehicle as the sanitizing mechanism moves from the first sanitizing position to the second sanitizing position.

8. The retractable sanitizing apparatus of claim 7, wherein the linkage member comprises an arm having one or more joints for pivoting the sanitizing mechanism from the stowed position to one of the first sanitizing position and the second sanitizing position.

9. The retractable sanitizing apparatus of claim 1, wherein:
the surface of the vehicle is the door of the vehicle; and
the sanitizing mechanism traverses the door in a vehicle vertical direction as the sanitizing mechanism moves from the first sanitizing position to the second sanitizing position.

10. The retractable sanitizing apparatus of claim 9, wherein:
the sanitizing mechanism comprises:
a first sanitizing mechanism portion;
a second sanitizing mechanism portion; and
the first sanitizing mechanism portion is temporarily separable from the second sanitizing mechanism portion as the sanitizing mechanism moves from the second sanitizing position toward the first sanitizing position and contacts an obstacle.

11. The retractable sanitizing apparatus of claim 10, wherein:
the first sanitizing mechanism portion comprises a first magnet; and
the second sanitizing mechanism portion comprises a second magnet for attaching to the first magnet when the sanitizing mechanism is not in contact with the obstacle.

* * * * *

UNITED STATES PATENT AND TRADEMARK OFFICE
CERTIFICATE OF CORRECTION

PATENT NO. : 12,071,109 B2  
APPLICATION NO. : 17/235249  
DATED : August 27, 2024  
INVENTOR(S) : Goemer et al.

Page 1 of 1

It is certified that error appears in the above-identified patent and that said Letters Patent is hereby corrected as shown below:

In the Drawings

In drawing sheet(s) 1 of 4, figure 1, and on the Title Page, the illustrative print figure, delete " 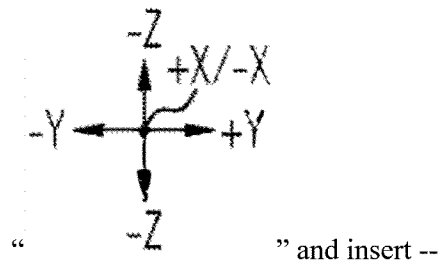 " and insert -- 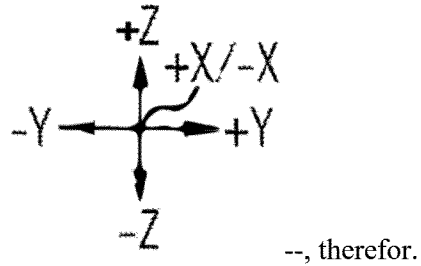 --, therefor.

In drawing sheet(s) 2 of 4, figure 2, delete " 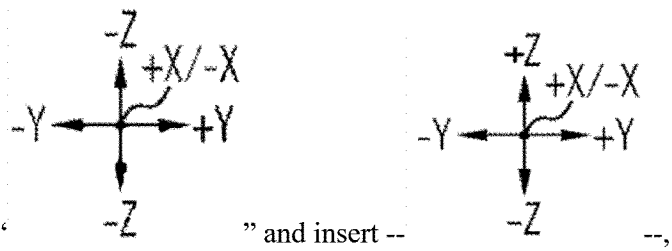 " and insert -- 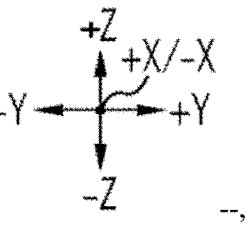 --, therefor.

Signed and Sealed this  
Thirty-first Day of December, 2024

Derrick Brent  
*Acting Director of the United States Patent and Trademark Office*